(12) United States Patent
Leussler et al.

(10) Patent No.: US 10,925,539 B2
(45) Date of Patent: Feb. 23, 2021

(54) PATIENT HEADPHONES WITH INTEGRATED SENSOR SYSTEM

(71) Applicant: KONINKLIJKE PHILIPS N.V., Eindhoven (NL)

(72) Inventors: Christoph Leussler, Eindhoven (NL); Daniel Wirtz, Eindhoven (NL); Sascha Krueger, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 235 days.

(21) Appl. No.: 15/522,331

(22) PCT Filed: Nov. 13, 2015

(86) PCT No.: PCT/EP2015/076506
§ 371 (c)(1),
(2) Date: Apr. 27, 2017

(87) PCT Pub. No.: WO2016/075270
PCT Pub. Date: May 19, 2016

(65) Prior Publication Data
US 2017/0311887 A1   Nov. 2, 2017

(30) Foreign Application Priority Data
Nov. 14, 2014  (EP) ..................... 14193168

(51) Int. Cl.
*A61B 5/00* (2006.01)
*A61B 5/1455* (2006.01)
(Continued)

(52) U.S. Cl.
CPC .......... *A61B 5/6803* (2013.01); *A61B 5/0059* (2013.01); *A61B 5/0077* (2013.01);
(Continued)

(58) Field of Classification Search
CPC . A61B 5/0059; A61B 5/02416; A61B 5/7285; A61B 5/6803; A61B 5/6815; A61B 5/1455; G01R 33/5673
See application file for complete search history.

(56) References Cited

U.S. PATENT DOCUMENTS 5,273,041 A * 12/1993 Richards ................ A61B 5/055
600/411
6,094,591 A * 7/2000 Foltz ...................... G01R 33/54
324/306

(Continued)

FOREIGN PATENT DOCUMENTS

WO   2009001449 A1   8/2010
WO   2011033422 A1   3/2011

OTHER PUBLICATIONS

Nikkei Electronics, Japan, Nikkei BP, Oct. 31, 2011, No. 1068, pp. 58-60 (no translation available).

(Continued)

*Primary Examiner* — Keith M Raymond
*Assistant Examiner* — Milton Truong

(57) ABSTRACT

Patient headphones (50) for use in a medical scanning modality, comprising a frame member (52), two ear cups (54) that, in an operational state of the patient headphones (50), are arranged to be in contact with one of the patient's ears, and a sensor system (60), the sensor system (60) including optical emitters (64) that are configured for directing electromagnetic radiation to a portion of the patient's skin, and optical sensors (68) that are configured for receiving the electromagnetic radiation being returned from the portion of the patient's skin, and for providing an output signal that corresponds to the received electromagnetic radiation, wherein the output signal is indicative of at least one physiological parameter of the patient and serves as a basis for determining the at least one physiological param- (Continued)

eter of the patient; —a patient headphones system (48) for use in a medical scanning modality (10), comprising an embodiment of such patient headphones (50) and a data acquisition and analysis unit (76) that is configured to acquire output signals of the optical sensors (68) and to analyze the acquired output signals by applying pre-determined criteria related to the output signals, and to provide a trigger output signal (80) if one of the pre-determined criteria is fulfilled; —a medical scanning modality (10) that is configured for contact-free acquisition of scanning data of at least a portion of a subject of interest (20), in particular a patient, comprising an embodiment of such patient headphones system (48), wherein the medical imaging modality (10) is in particular formed as a magnetic resonance imaging system.

17 Claims, 4 Drawing Sheets

(51) Int. Cl.
*A61B 5/024* (2006.01)
*G01R 33/28* (2006.01)
*G01R 33/567* (2006.01)

(52) U.S. Cl.
CPC ........ *A61B 5/02416* (2013.01); *A61B 5/1455* (2013.01); *A61B 5/6815* (2013.01); *A61B 5/72* (2013.01); *A61B 5/7285* (2013.01); *G01R 33/283* (2013.01); *G01R 33/5673* (2013.01)

(56) References Cited

U.S. PATENT DOCUMENTS

| | | | |
|---|---|---|---|
| 6,816,266 B2 | 11/2004 | Varshneya | |
| 2005/0107681 A1* | 5/2005 | Griffiths | A61B 5/0046 600/410 |
| 2006/0276700 A1* | 12/2006 | O'Neil | A61B 5/6814 600/344 |
| 2007/0032274 A1* | 2/2007 | Lee | H04R 1/1025 455/575.2 |
| 2008/0013777 A1* | 1/2008 | Park | A61B 5/0059 381/384 |
| 2008/0132798 A1* | 6/2008 | Hong | A61B 5/6815 600/508 |
| 2008/0177162 A1* | 7/2008 | Bae | A61B 5/02416 600/323 |
| 2010/0217139 A1 | 8/2010 | Pinter et al. | |
| 2011/0066027 A1 | 3/2011 | Schnell | |
| 2011/0074409 A1* | 3/2011 | Stoughton | G01R 33/5673 324/307 |
| 2011/0196211 A1* | 8/2011 | Al-Ali | A61B 5/14551 600/300 |
| 2013/0039509 A1* | 2/2013 | Chuang | A61B 5/0478 381/74 |
| 2013/0311176 A1* | 11/2013 | Brown | H04R 1/1091 704/233 |
| 2014/0058230 A1* | 2/2014 | Abdul-Hafiz | A61B 5/14552 600/324 |
| 2014/0058248 A1 | 2/2014 | Leussler | |
| 2014/0123980 A1 | 5/2014 | Rissacher et al. | |
| 2014/0192177 A1 | 7/2014 | Bartula et al. | |
| 2014/0213917 A1* | 7/2014 | Hobeika | A61B 5/02416 600/500 |
| 2014/0275970 A1* | 9/2014 | Brown | G01R 33/283 600/413 |
| 2014/0278220 A1* | 9/2014 | Yuen | G01B 21/16 702/150 |
| 2015/0100310 A1* | 4/2015 | Cha | G10L 21/0208 704/228 |
| 2015/0112153 A1* | 4/2015 | Nahum | A61B 5/6803 600/301 |

OTHER PUBLICATIONS

Julian Maclaren et al, Simultaneous monitoring of cardiac and respiratory signals using a markerless optical system, Dept. of Radiology, Stanford University, Stanford, CA, United StatesProc. Intl. Soc. Mag. Reson. Med. 22 (2014).

\* cited by examiner

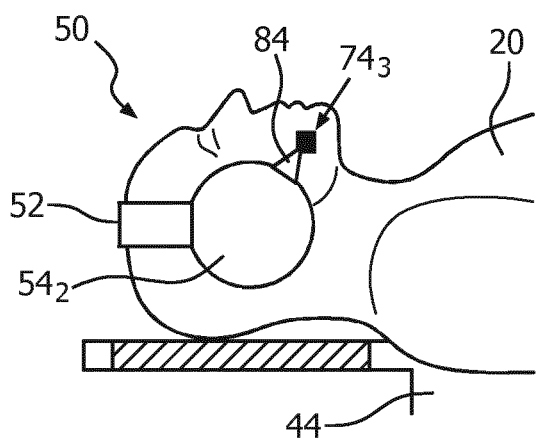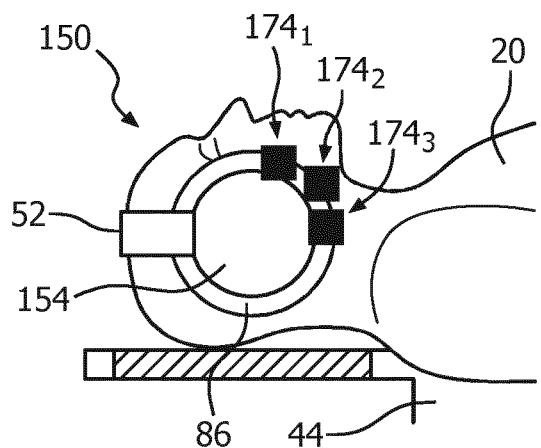
FIG. 4  FIG. 5
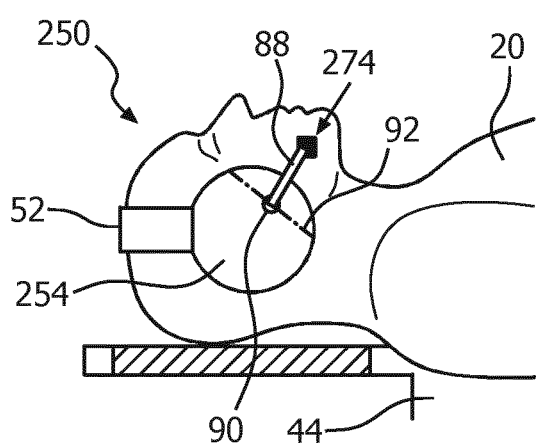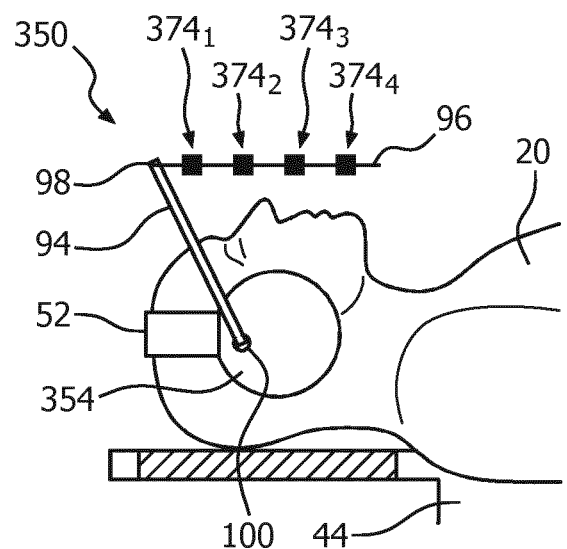
FIG. 6  FIG. 7

PATIENT HEADPHONES WITH INTEGRATED SENSOR SYSTEM

CROSS REFERENCE TO RELATED APPLICATIONS

This application is a U.S. national phase application of International Application No. PCT/EP2015/076506, filed on Nov. 13, 2015, which claims the benefit of EP Application Serial No. 14193168.3 filed on Nov. 14, 2014 and is incorporated herein by reference.

FIELD OF THE INVENTION

The invention pertains to patient headphones having a sensor system, for use in a medical scanning modality, in particular a magnetic resonance imaging system, a patient sensor system including such headphones and sensor system, a medical scanning modality, in particular a magnetic resonance imaging system, comprising such patient sensor system, and a method of determining, by using such patient sensor system, at least one physiological parameter of a patient to be examined by such medical scanning modality for gating a scanning process of the medical scanning modality.

BACKGROUND OF THE INVENTION

In the field of medical scanning, it is known to monitor physiological parameters of a patient such as, but not limited to, cardiac cycles and respiratory cycles, and to use the monitored physiological parameters for temporal control, for instance by gating and/or triggering, of a scanning process.

Determining physiological parameters during scanning examination is usually performed by means of suitable sensors requiring setting up on the patient. For instance, a conventional way of determining a respiratory waveform of the patient is by employing a respiration belt-type monitoring device which includes a respiration sensor that usually is attached to the thorax of the patient, and is held by a belt wound around the thorax.

In document WO 2011/033422 A1, a magnetic resonance imaging system is described that comprises a radio frequency coil unit for generating radio frequency pulses within an examination volume and/or for receiving magnetic resonance signals from an object position in the examination volume. It is further suggested therein to integrate into the radio frequency coil unit a setup of at least one physiological sensor for receiving physiological signals from the object. The physiological sensor uses the means for signal transmission already present for transmitting the received magnetic resonance signals from the radio frequency coil unit to a remote signal acquisition and processing hardware. Further, the US patent application US2014/0123980, discloses a patient head phones system that is fitted with a SpO$_2$ sensor the measure the user's oxygen saturation.

SUMMARY OF THE INVENTION

It is desirable to provide a physiological sensor for determining a physiological parameter of the patient for which a setting up on the patient can be omitted and that can be operated independent of any scanning unit of a medical scanning modality.

In one aspect of the present invention, the object is achieved by patient headphones for use in a medical scanning modality. The headphones comprise a frame member adapted to the shape of a patient's head, two ear cups that are attached to the frame member such that, in an operational state of the patient headphones, each of the ear cups is arranged to be in contact with one of the patient's ears, and a sensor system.

The sensor system includes at least one optical emitter that is temporarily fixedly attachable to one out of the frame member and the ear cups and is configured for directing electromagnetic radiation to a portion of the patient's skin. The sensor system further includes at least one optical sensor that is temporarily fixedly attachable to one out of the frame member and the ear cups and is configured for receiving at least a portion of the electromagnetic radiation being returned from the portion of the patient's skin. The at least one optical sensor is furthermore configured for providing an output signal that corresponds to the received electromagnetic radiation. The output signal of the at least one optical sensor is indicative of at least one physiological parameter of the patient and serves as a basis for determining the at least one physiological parameter of the patient.

The phrase "ear cups", as used in this application, shall be understood particularly to encompass circum-aural ear cups as well as supra-aural ear cups.

The phrase "optical emitter", as used in this application, shall be understood particularly as an emitter emitting electromagnetic radiation in the range encompassing the optical regime of electromagnetic waves visible to human beings, as well as the regime of infrared radiation (Near Infrared (NIR), Mid Infrared (MIR) and Far Infrared (FIR)) and the regime of radio frequency radiation of extremely high frequency (EHF), i.e. a frequency bandwidth reaching from visible light down to radio frequencies as low as 30 GHz. The optical sensor is understood to be adapted to sense the electromagnetic radiation emitted by the optical emitter.

The phrase "physiological parameter", as used in this application, shall be understood particularly as a physical measure characterizing the function of at least a portion of an individual subject of interest, and shall in particular encompass parameters such as, but not limited to, respiration cycle parameters and cardiac cycle parameters.

The phrase "temporarily fixedly attachable", as used in this application, shall be understood particularly as an option to be attached in a fixed configuration for a time desired by an operator, and to be transferable from one fixed configuration to another fixed configuration by the operator in a non-destructive way.

An object of the present invention is also to provide for triggering of the scanning modality on the basis of one or more physiological parameters of the patient to be examined. Notably, a further object of the invention is to achieve this triggering without the need of additional cabling in the medical scanning modality. To achieve this object, the patient headphones system further comprises a data acquisition and analysis unit that is configured to acquire output signals of the optical sensors and to analyze the acquired output signals by applying pre-determined criteria related to the output signals, and to provide a trigger output signal if one of the pre-determined criteria is fulfilled.

One advantage of the patient headphones lies in that the at least one physiological parameter can be determined at least with reduced setup time of a sensor system and that it can be operated independent of any scanning unit of the medical scanning modality the patient headphones are used for.

Another advantage of the patient headphones lies in that the frame member and the ear cups provide to the fixedly attached sensor system a reference frame that travels with the patient wearing the patient headphones. In this way, a definite and robust spatial relationship between the patient and the sensor system can be established. The effect of this is that the at least one physiological parameter can be determined from motions of a portion of the patient relative to the balance of the patient and irrespective of any motion of the patient as a whole. This is especially advantageous as the quantity to be measured is not determined as a difference of two substantially equally large quantities, a condition that is known to result in high precision requirements.

Yet another advantage lies in that existing patient headphones that are already available for use in a medical scanning modality can be readily modified as patient headphones pursuant to the invention, so that, in general, parts and costs can be saved.

In a preferred embodiment, the patient headphones further include
  at least one loudspeaker, and
  an audio receiving member that is configured for receiving an audio signal that at least forms the basis for driving the at least one loudspeaker.

In this case, each of the ear cups is arranged to contact one of the patient's ears in such a way that the patient is enabled to hear an acoustic signal emitted by the at least one loudspeaker. Preferably, the audio signal may be provided to the audio receiving member via an electrical or a pneumatic path or a combination of both.

In one embodiment, the audio receiving member may be designed as a conventional audio plug member that is configured to receive an analog or digital electric audio signal for driving the at least one loudspeaker.

In one embodiment, the audio receiving member may be designed as a receiver unit that is configured for wirelessly receiving radio frequency signals that represent the audio signal.

In one embodiment, a loudspeaker is installed in each ear cup of the ear cups of the patient headphones. In this case, each of the ear cups is arranged to contact one of the patient's ears in such a way that the patient is enabled to hear an acoustic signal emitted by each one of the loudspeakers. This embodiment of the ear cups and the latter one enable one-way communication from medical staff to the patient.

In one embodiment, the patient headphones are further equipped with a microphone to form a complete headset to enable mutual communication between the patient and medical staff.

In another preferred embodiment of the patient headphones, the at least one optical sensor is designed as a digital camera. The phrase "digital camera", as used in this application, shall be understood particularly to encompass a digital single-shot camera or a digital video camera, both of which may be RGB input devices or IR (infrared)-sensitive, depending on the actual embodiment of the optical emitter.

In this way, digital data representing the output signal of the optical sensor are readily available for determining the at least one physiological parameter of the patient.

In a preferred embodiment, the at least one optical emitter and the at least one optical sensor are designed to form an integrated unit such that a mutual relative spatial relationship between the at least one optical emitter at the at least one optical sensor is fixed. In this way, it can be ensured that the amount of electromagnetic radiation that is returned from the portion of the patient's skin to the at least one optical sensor is sufficient for a large number of patient positions.

Preferably, the at least one optical emitter and the at least one optical sensor are installed in a common housing.

In yet another preferred embodiment, the patient headphones comprise a plurality of optical emitters and a plurality of optical sensors. In this way, the patient headphones provide several options of determining a physiological parameter from which an operator can select, according to the intended examination.

Preferably, the optical emitters and optical sensors are temporarily fixedly attached to one out of the frame member and the ear cups such that their optical axis is directed, in an operational state, to one out of the patient's forehead, the patient's cheeks and patient's temples as a default position. In this way, the patient headphones can quickly be put to operation without any further required adjustment.

In another preferred embodiment, one of the optical emitters and one of the optical sensors are commonly installed in at least one of the ear cups of the headphones such that their optical axes are directed to the skin of the patient's ear.

In another preferred embodiment, the patient headphones further comprise a holder member that is attached to the frame member and that is configured for holding the optical sensor or the optical sensors, respectively. The holder member provides additional options for temporarily fixedly attaching and directing optical sensors towards skin parts of the patient's head. Preferably, the holder member is substantially rigid and includes at least one articulation link for adjusting a position of the holder member relative to the frame member, and a locking member for locking the articulation link in a desired position. Preferably, the locking member is designed to hold the desired position by friction. In particular, the locking member and/or the holder member may be designed as a gooseneck holder.

In another preferred embodiment, the patient headphones further include electromagnetic induction means that are configured for powering the patient headphones when positioned in the proximity of corresponding powered induction means, by transferring electric power in a wireless way.

In this way, the patient headphones can readily be provided with electric power, omitting cumbersome cabling that needs the attendance of an operator during positioning the patient so as to not interfere with optical emitters or optical sensors.

Cumbersome cabling for data transmission and potential interference with optical emitters or optical sensors can also at least be reduced if the optical sensor is configured or the optical sensors are configured, respectively, to transmit the output signal by using one out of a radio frequency data emitter or an optical data cable.

In another aspect of the present invention, a patient headphones system for use in a medical scanning modality is provided. The patient headphones system includes an embodiment of the patient headphones disclosed herein.

In yet another aspect of the present invention, a medical scanning modality is provided that is configured for contact-free acquisition of scanning data of at least a portion of a subject of interest, in particular a patient.

The medical scanning modality includes
  a scanning unit having an examination space that is provided for arranging at least the portion of the subject of interest within,
  a control unit that is configured for controlling functions of the medical imaging modality,
  a signal processing unit that is configured to generate scanning images from the acquired scanning data, and an embodiment of the patient sensor system as disclosed herein.

By furnishing the medical scanning modality with an embodiment of the patient sensor system, the respective advantages described for the various embodiments can be accomplished.

In particular, the contemplated medical scanning modalities include, but are not limited to, a magnetic resonance imaging (MRI) apparatus, especially of the bore-type, a computer tomography (CT) apparatus, a single-photon emission computed tomography (SPECT) apparatus, a Positron Emission Tomography (PET) apparatus or an image-guided therapy system such as an MR-LINAC system, an MR Hyperthermia therapy system or an MR-guided High-Intensity Focused Ultrasound (HIFU) system.

In a preferred embodiment, the medical scanning modality is formed as a magnetic resonance imaging system configured for acquiring magnetic resonance images of at least a portion of a subject of interest, usually a patient. The scanning data are formed by magnetic resonance signals and the generated scanning images are formed by magnetic resonance images.

The scanning unit further includes
- a main magnet provided for generating a static magnetic field B0 at least in the examination space, wherein the examination space is provided in a bore region of the main magnet;
- a magnetic gradient coil system configured for generating gradient magnetic fields superimposed to the static magnetic field B0;
- at least one radio frequency antenna device that is configured for applying a radio frequency excitation field B1 to nuclei of or within the portion of the subject of interest for magnetic resonance excitation; and
- at least one radio frequency antenna device that is configured for receiving magnetic resonance signals from the nuclei of or within the portion of the subject of interest that have been excited by applying the radio frequency excitation field $B_1$.

In a preferred embodiment of the medical scanning modality, the control unit is configured to receive the trigger output signal and to control a scanning process being carried out by the medical scanning modality by using the received trigger output signal for gating and/or triggering the acquisition of scanning data. This enables acquiring scanning data that are assigned to a specified value or a specified range of values of the at least one physiological parameter, corresponding to a specific phase of the physiological function such as, but not limited to, a specific phase of the cardiac cycle or a specific phase of the respiratory phase of the patient.

In another aspect of the invention, a method is provided for determining, by using an embodiment of the patient headphones system as disclosed herein, at least one physiological parameter of a patient to be examined by a medical scanning modality for gating a scanning process of the medical scanning modality.

The method comprises steps of
- carrying out a calibration procedure by acquiring an output signal or output signals of the optical sensor or the optical sensors of the patient sensor system that is or are indicative of the at least one physiological parameter,
- determining values related to the output signal or the output signals that are to be used as threshold values,
- defining at least one criterion related to the output signal or the output signals with regard to the determined threshold values,
- acquiring an output signal or output signals of the optical sensor or the optical sensors,
- applying the defined at least one criterion to the output signal or the output signals acquired,
- generating a trigger output signal if the at least one defined criterion is fulfilled, and
- gating the scanning process by making use of generated trigger output signals.

In yet another aspect of the present invention, a software module is provided for carrying out steps of an embodiment of the disclosed method of determining, by using an embodiment of the patient sensor system as disclosed herein, at least one physiological parameter of a patient to be examined by a medical scanning modality for gating a scanning process of the medical scanning modality. The method steps to be conducted are converted into a program code of the software module, wherein the program code is implementable in a memory unit of the medical scanning modality and is executable by a processor unit of the medical scanning modality. The processor unit may be the processor unit of the control unit that is customary for controlling functions of the medical scanning modality. The processor unit may, alternatively or supplementary, be another processor unit that is especially assigned to execute at least some of the method steps.

At least one physiological parameter like breathing rate or heart rate is determined by the measurement by the optical sensor system in the head phones system. In practice, the patient's face is not covered by clothes, cameras integrated in a headset are positioned almost equally on different patients allowing for generating robust and reliable signals to trigger an imaging system. The modulated reflected optical or IR signal is analyzed and a suitable algorithm provides trigger signals to the imaging system. Furthermore other tasks may be fulfilled using an array of optical sensors such as control of bulk motion, feedback for functional imaging, determination of the status of the patient and correlations between these.

The software module can enable a robust and reliable execution of the method and can allow for a fast modification of method steps.

BRIEF DESCRIPTION OF THE DRAWINGS

These and other aspects of the invention will be apparent from and elucidated with reference to the embodiments described hereinafter. Such embodiment does not necessarily represent the full scope of the invention, however, and reference is made therefore to the claims and herein for interpreting the scope of the invention.

In the drawings.

DETAILED DESCRIPTION OF EMBODIMENTS

Figure 1:
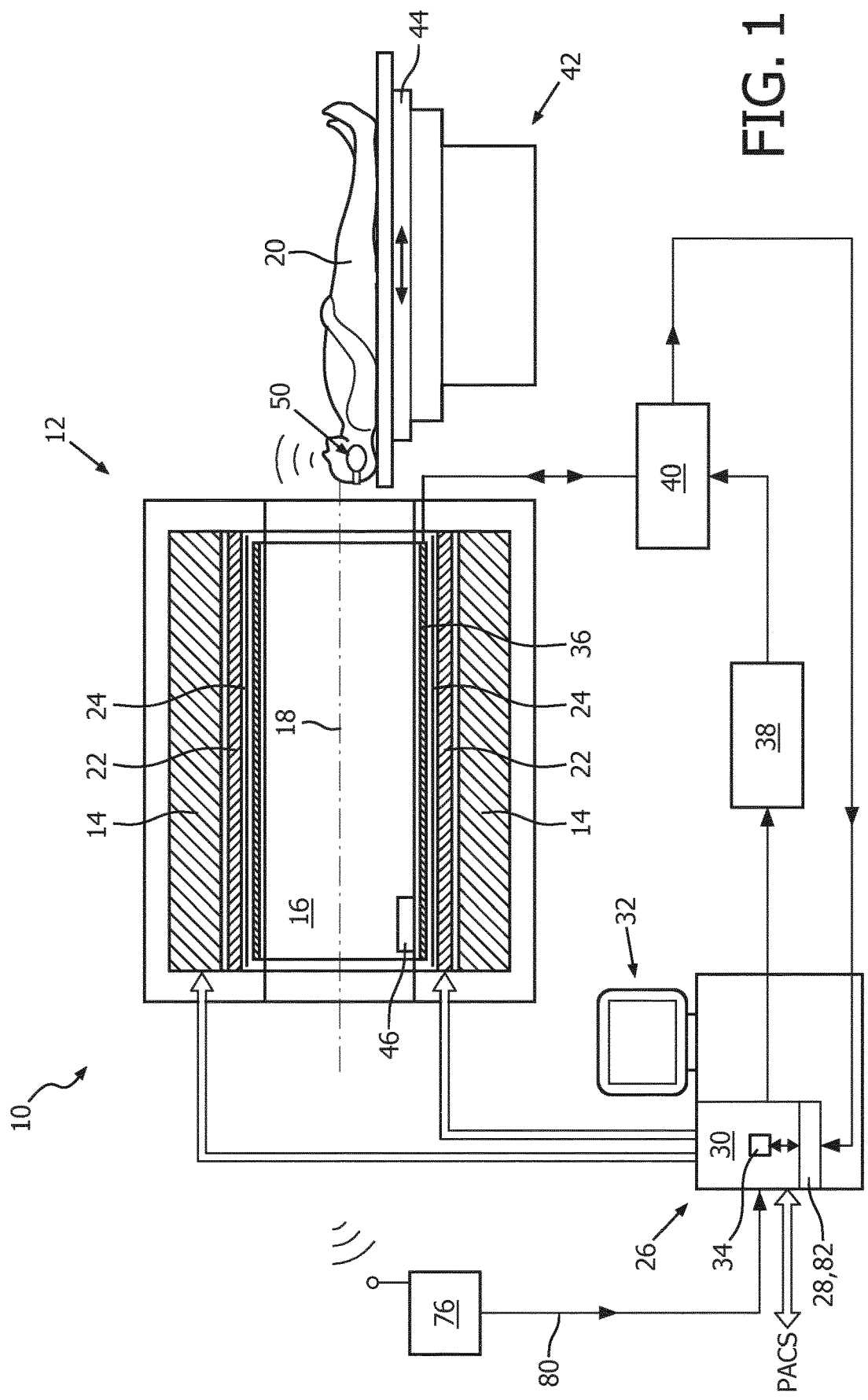
FIG. 1 shows a schematic illustration of a part of an embodiment of medical imaging modality in accordance with the invention, designed as a magnetic resonance imaging system, FIG. 2 schematically illustrates a front view of a configuration of the patient headphone system in accordance with the invention and pursuant to FIG. 1, attached at a patient in an operational state, FIG. 3 schematically illustrates a side view of the configuration pursuant to FIG. 2, FIG. 4 schematically shows a detail of a front view of a configuration of the embodiment of patient headphones pursuant to FIGS. 2 and 3, FIG. 5 schematically shows a detail of a front view of a configuration of an alternative embodiment of patient headphones in accordance with the invention, attached at a patient in an operational state, FIG. 6 schematically shows a detail of a front view of a configuration of another alternative embodiment of patient headphones in accordance with the invention, attached at a patient in an operational state, FIG. 7 schematically shows a detail of a front view of a configuration of yet another alternative embodiment of patient headphones in accordance with the invention, attached at a patient in an operational state.

FIG. 1 shows a schematic illustration of a part of an embodiment of a medical imaging modality 10 in accordance with the invention that is configured for contact-free acquisition of scanning data of at least a portion of a subject of interest 20, usually a patient. The medical imaging modality 10 is designed, without limitation for the scope of protection, as a magnetic resonance imaging system. Patient headphones and a patient headphones system, as described for use in this embodiment of the medical imaging modality 10, are also applicable in other medical imaging modalities, such as positron emission tomography devices or computer tomography devices, as will be appreciated to those skilled in the art.

Acquired scanning data are formed by magnetic resonance signals and generated scanning images are formed by magnetic resonance images.

The magnetic resonance imaging system is thus configured for contact-free acquisition of magnetic resonance images of at least a portion of the subject of interest 20. To this end, the magnetic resonance imaging system comprises a scanning unit 12 with a main magnet 14 provided for generating a static magnetic field $B_0$. The main magnet 14 has a central bore that provides an examination space 16 around a center axis 18 for the subject of interest 20 to be positioned within. The main magnet 14 is configured to generate the static magnetic field $B_0$ at least in the examination space 16. The static magnetic field $B_0$ defines an axial direction of the examination space 16, aligned in parallel to the center axis 18.

The magnetic resonance imaging system comprises an examination table 42 having a slidably arranged table top 44 for supporting the subject of interest 20 prior and after an examination outside the examination space 16 as well as while being arranged inside the examination space 16 during the examination.

The magnetic resonance imaging system further comprises a magnetic gradient coil system 22 with magnetic gradient coils provided for generating gradient magnetic fields superimposed to the static magnetic field $B_0$. The magnetic gradient coils are concentrically arranged within the bore of the main magnet 14, as is known in the art.

Further, the magnetic resonance imaging system includes a radio frequency antenna device 36 designed as a whole-body coil that is provided for applying a radio frequency magnetic field $B_1$ to the examination space 16 during radio frequency transmit phases to excite nuclei of or within the subject of interest 20. The radio frequency antenna device 36 is also configured for receiving magnetic resonance signals during radio frequency receive phases from the nuclei of or within the portion of the subject of interest 20 that have been excited by applying the radio frequency excitation field $B_1$. In an operational state of the magnetic resonance imaging system, radio frequency transmit phases and radio frequency receive phases are taking place in a consecutive manner. The radio frequency antenna device 36 is arranged concentrically within the bore of the main magnet 14. As is well known in the art, a cylindrical metal radio frequency shield 24 is arranged concentrically between the magnetic gradient coils of the magnetic gradient coil system 22 and the radio frequency antenna device 36.

The magnetic resonance imaging system further comprises a control unit 26 provided for controlling functions of the magnetic resonance imaging system. The control unit 26 comprises a human interface device for displaying and controlling purposes that is designed as a touch screen device 32.

Furthermore, the magnetic resonance imaging system includes a radio frequency transmitter unit 38 that is connected to and controlled by the control unit 26. The radio frequency transmitter unit 38 is provided to feed radio frequency power of a magnetic resonance radio frequency to the radio frequency antenna device 36 via a radio frequency switching unit 40 during the radio frequency transmit phases. During radio frequency receive phases, the radio frequency switching unit 40 directs the magnetic resonance signals from the radio frequency antenna device 36 to a signal processing unit 34 residing in the control unit 26. The signal processing unit 34 is configured for processing acquired magnetic resonance signals to generate scanning images represented by magnetic resonance images of the portion of the subject of interest 20 from the acquired scanning data represented by the magnetic resonance signals. This technique is well known to those skilled in the art and thus need not be described in further detail herein.

The control unit 26 further comprises a digital memory unit 28 for at least temporarily storing the generated magnetic resonance images. The magnetic resonance imaging system is connected to a Picture Archiving and Communication System (PACS) of the medical center that it is installed in via a data connection. In this way, data can be transferred between the magnetic resonance imaging system and the PACS.

Moreover, the magnetic resonance imaging system includes a patient headphones system 48 for determining a physiological parameters of the subject of interest 20 to be examined by use of the magnetic resonance imaging system.

The patient headphones system 48 includes patient headphones 50 and a data acquisition and analysis unit 76.

Figure 2:
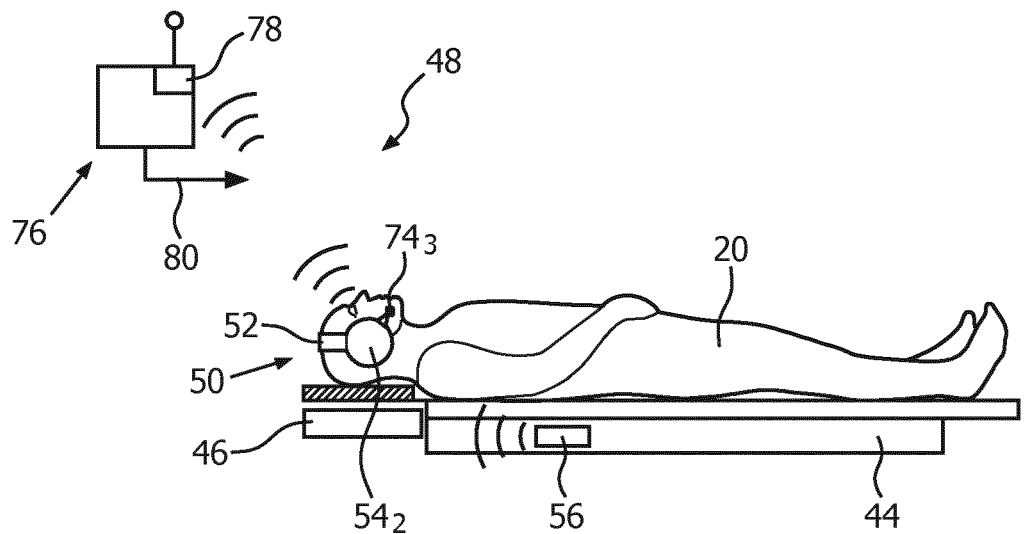
Figure 3:
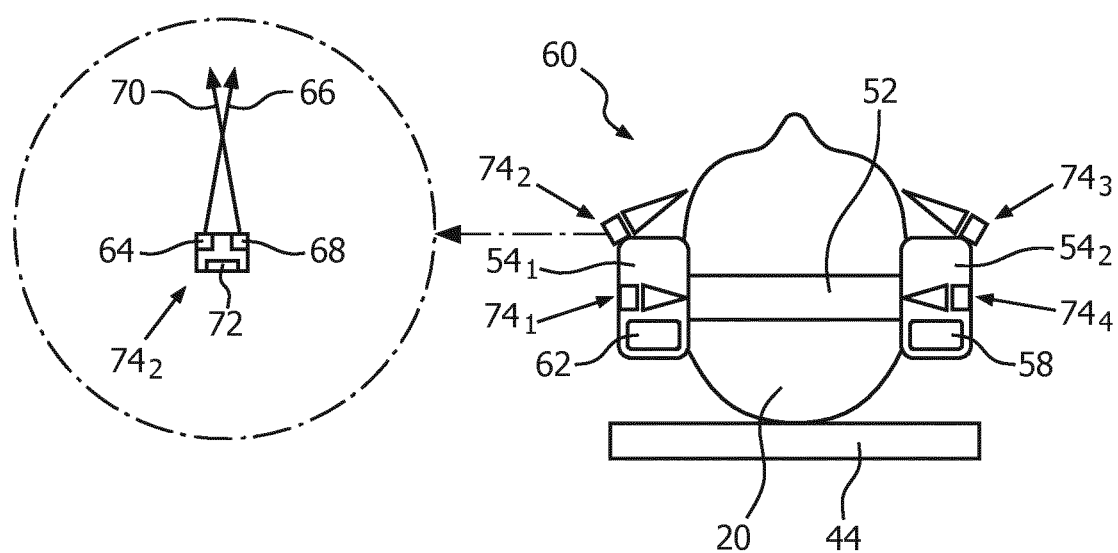

The patient headphones 50 comprise a frame member 52 designed in the conventional U-shape that is adapted to a shape of the patient's head and made from an elastic plastic material (FIG. 2). A resilient force provided by the elastic frame member 52 ensures that, in an operational state of the patient headphones 50, each of two ear cups $54_1$, $54_2$ that are attached to the frame member 52 is reliably in contact with one of the patient's ears (FIG. 3).

The patient headphones 50 further comprise an audio receiving member 58 designed as a wireless receiver unit that is connected to a digital-to-analog converter, both of which are integrated into one of the ear cups $54_1$, $54_2$. The audio receiving member 58 is configured for receiving radio frequency signals from a radio frequency audio transmitter 56 formed by a Bluetooth® master device that is integrated in the table top 44 (FIG. 2). The radio frequency signals represent an audio signal and are converted by the digitalto-analog converter into analog voltage signals for driving at least one loudspeaker that is installed in one of the ear cups $54_1$, $54_2$ (FIG. 3).

Although in this specific embodiment radio frequency signals are provided to the audio receiving member 58 by a Bluetooth® master device, it will be appreciated by those skilled in the art that the signals representing an audio signal may be provided as well by other suitable link devices such as a microwave link device or an optical link device, wherein the audio receiving member would have to be equipped with appropriate receiving means.

Furthermore, the patient headphones 50 include a sensor system 60. The sensor system 60 comprises a plurality of identical optical emitters 64 and a plurality of identical optical sensors 68. Each optical sensor 68 of the plurality of optical sensors 68 is designed as a digital camera.

Each optical emitter 64 of the plurality of optical emitters 64 is configured for directing electromagnetic radiation to a portion of the patient's skin. Each optical sensor 68 of the plurality of optical sensors 68 is configured for receiving at least a portion of the electromagnetic radiation being returned from the portion of the patient's skin.

The optical emitters 64 of the plurality of optical emitters 64 and the optical sensors 68 of the plurality of optical sensors 68 are designed to form integrated units $74_1$-$74_4$ such that a mutual relative spatial relationship between the optical emitter 64 and the optical sensor 68 of each integrated unit $74_1$-$74_4$ is fixed. As indicated in FIG. 3, an optical axis 66 of the optical emitter 64 and an optical axis 70 of the optical sensor 68 intersect in a distance to the integrated unit $74_i$, i=1-4 with a high probability of being in close proximity to an average patient's head.

Then, the patient headphones 50 include electromagnetic induction means 62 that are configured for powering the patient headphones 50 in a wireless way. This is accomplished by positioning the electromagnetic induction means 62 of the patient headphones 50 close to and above corresponding electromagnetic induction means 46 that are permanently installed in one end of the table top 44 of the patient examination table 42, below a portion of the table top 44 that is provided for supporting the patient's head (FIG. 2).

As is shown in FIG. 3, one integrated unit $74_1$, $74_4$ each, comprising an optical emitter 64 and an optical sensor 68, is permanently installed in each ear cup $54_1$, $54_2$ of the patient headphones 50. Their optical axes 66, 70 are, in the operational state of the patient headphones 50, substantially directed towards one of the patient's ears.

Two more integrated units $74_2$, $74_3$ are temporarily fixedly attached to the ear cups $54_1$, $54_2$ by holder members designed as fixation clamps 84, one integrated unit $74_2$, $74_3$ being attached to each ear cup $54_1$, $54_2$ (FIG. 4). The optical axes 66, 70 of the optical emitter 64 and the optical sensor 68 of these integrated units $74_2$, $74_3$ are substantially directed towards a region in which the left and the right cheek of the patient are supposed to be disposed in the operational state of the patient headphones 50. By changing a position of the fixation clamps 84 on the ear cups $54_1$, $54_2$ by an operator, the integrated units $74_2$, $74_3$ can be directed towards other parts of the patient's head, such as the cheeks or the forehead.

Each optical sensor 68 of the plurality of optical sensors 68 is configured for providing an output signal that corresponds to the received electromagnetic radiation, returned from the portion of the patient's skin that has been illuminated by one of the optical emitters 64. Each output signal is indicative of a physiological parameter of the patient and serves as a basis for determining the physiological parameter of the patient. In this specific embodiment, the physiological parameter is the cardiac cycle of the patient, which is determined from the output signals of the optical sensors 68 that are indicative of changes of the skin color of the patient. For this purpose, the optical emitters 64 are configured to emit light of several wavelengths for which oxygen-rich blood and oxygen-poor blood have different absorption rates. The method for determining the cardiac cycle of the patient is therefore similar to methods known from reflectance pulse oximetry.

Each optical sensor 68 of the plurality of optical sensors 68 is equipped with a radio frequency data emitter 72 (FIG. 3) based on Bluetooth® protocol, and is configured to transmit its output signal in a wireless way to the data acquisition and analysis unit 76 (FIG. 2). The radio frequency data emitters 72 of the optical sensors 68 are powered by the electromagnetic induction means 62 as described before.

The data acquisition and analysis unit 76 is furnished with a radio frequency data receiver 78 based on Bluetooth® protocol, and is configured to acquire the output signals of the optical sensors 68 and to analyze the acquired output signals by applying pre-determined criteria related to the output signals. The data acquisition and analysis unit 76 is further configured to provide a trigger output signal 80 (FIG. 1) if one of the pre-determined criteria is fulfilled, which the control unit 26 of the magnetic resonance imaging system is configured to receive and to use for controlling a scanning process to be carried out, as we will be described in more detail in the following.

Although the radio frequency antenna device 36 is described in this specific embodiment as a transmit/receive radio frequency coil, it is also contemplated to apply the invention to magnetic resonance imaging systems comprising radio frequency antenna devices configured for receiving magnetic resonance signals which are designed as local coils, as is well known in the art. The magnetic resonance imaging system may, for instance, employ a head coil that is compatible with the patient headphones of the invention. In this case, the head coil and surrounding surfaces are covered with a surface material that is highly absorptive with regard to the electromagnetic radiation emitted by the optical emitters, so as to not affect the measurement of the optical sensor by reflected patterns.

Figure 8:
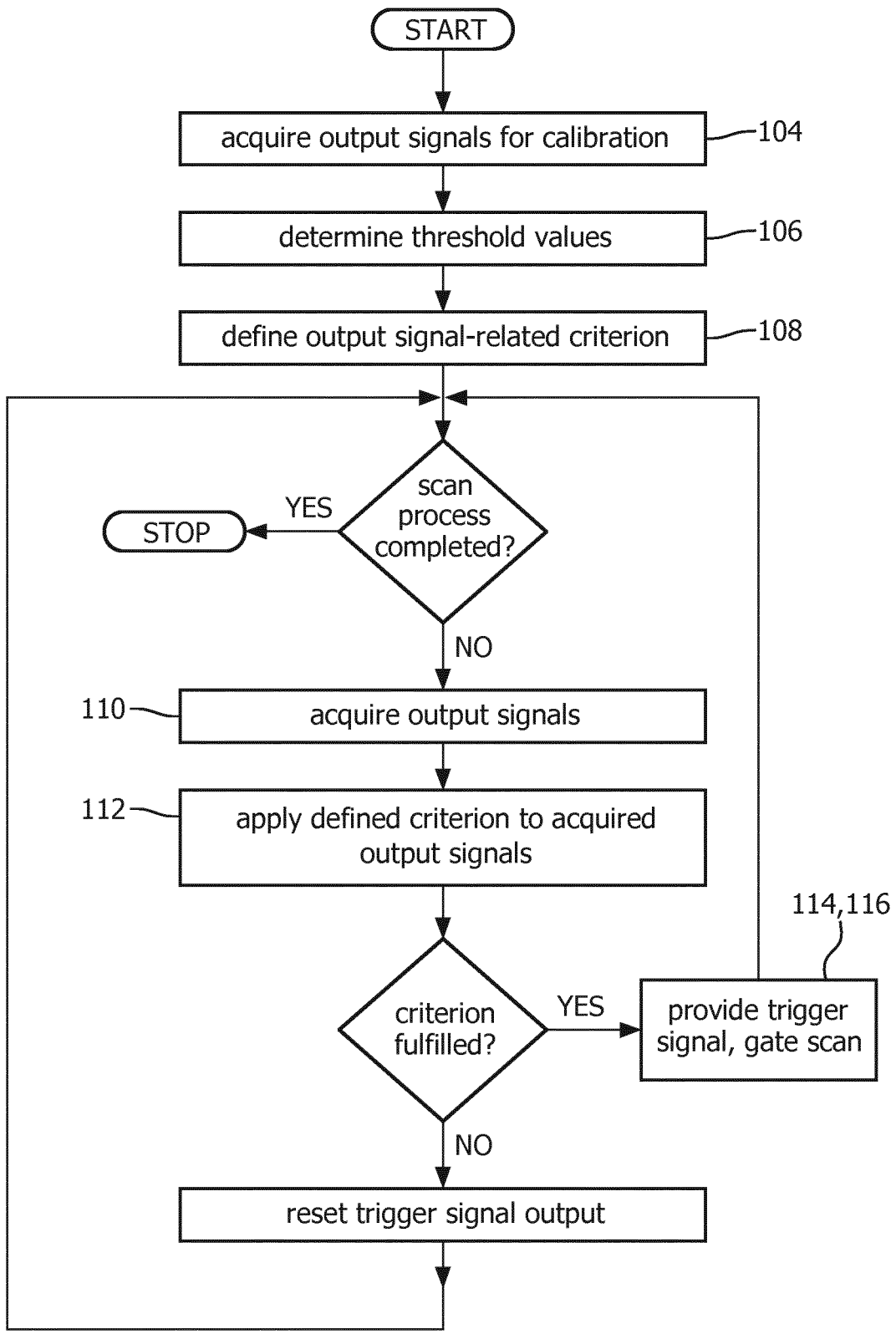
FIG. 8 shows a flow chart of an embodiment of the method in accordance with the invention.

Next, an embodiment of a method for determining, by using the embodiment of the patient headphones system 48 described before, a physiological parameter, namely the cardiac cycle, of the patient to be examined by the magnetic resonance imaging system for gating a scanning process of the magnetic resonance imaging system is described. A flow chart of the method is given in FIG. 8. In preparation of carrying out the method, it shall be understood that all involved units and devices are in an operational state and configured as illustrated in FIG. 1.

In order to be able to carry out the method, the control unit 26 comprises a software module 82 (FIG. 1). The method steps to be conducted are converted into a program code of the software module 82, wherein the program code is implemented in the digital memory unit 28 of the control unit 26 and is executable by the processor unit 30 of the control unit 26. Alternatively, the patient headphone system 48 may include a control unit having a digital memory unit and a processor unit, for instance within the data acquisition and analysis unit 76, the software module may reside in the digital memory unit of the control unit of the patient headphone system 48, and the processor unit of the patient headphone system 48 may be especially configured to carry out the method.

It shall be understood that the magnetic resonance imaging system is in a ready-to-operate state and that the subject of interest 20 is lying in a dorsal position on the examination table 42, as indicated in FIG. 1.

In a first step 104, a calibration procedure is carried out by acquiring output signals of the optical sensors $68_1$-$68_4$ of the patient sensor system 48 that are indicative of the physiological parameter given by the cardiac cycle.

In the next step 106, values related to the output signals that are to be used as threshold values are determined. In this embodiment, the values are given by the maximum magnitudes of the output signals, which are averaged over a plurality of cardiac cycles to obtain a mean amplitude.

In the following step 108 of the method, a criterion related to the output signals with regard to the determined threshold values is defined. In this embodiment, the criterion is defined for the output signal to be at least 80% of the mean amplitude.

In a series of steps which are carried out in a repetitive way at least during the scanning process, output signals of the optical sensors $68_1$-$68_4$ are acquired 110, the defined criterion is applied 112 to the output signals, and a trigger output signal 80 is generated 114 if the defined criterion is fulfilled. The control unit 26 of the magnetic resonance imaging system receives the trigger output signals 80 and uses them for gating 116 the scanning process.

In this way, quasi-continuous feedback on the physiological parameter obtained by the patient headphones system 48 is provided to the control unit 26 of the magnetic resonance imaging system for the purpose of controlling a timing of the scanning process.

In the following, several alternative embodiments of the patient headphones in accordance with the invention, for use in the medical scanning modality designed as a magnetic resonance imaging system are disclosed. The individual alternative embodiments are described with reference to a particular figure and are identified by a prefix number of the particular alternative embodiment, beginning with "1". Features whose function is the same or basically the same in all embodiments are identified by reference numbers made up of the prefix number of the alternative embodiment to which it relates, followed by the number of the feature. If a feature of an alternative embodiment is not described in the corresponding figure depiction, or a reference number mentioned in a figure depiction is not shown in the figure itself, the description of a preceding embodiment should be referred to.

Only features differing from the embodiment pursuant to FIG. 4 will be described. For features of the alternative embodiments that are not described hereinafter, reference is made to the description of the first embodiment.

The alternative embodiments comprise a holder member or holder members that is or that are attached to one out of the frame member 52 and the ear cups 54. The holder members are configured for holding optical sensors 68 or integrated units 74, respectively. For alternative embodiments in which the holder member or the holder members are shown to be attached at the ear cups 54, it is as well contemplated that they may be attached to the frame member 52, and vice versa.

The first alternative embodiment of patient headphones 150 is shown in FIG. 5. The patient headphones 150 include two holder members (only one holder member on right patient side shown, other holder member is identically designed and furnished) that are designed as ring-shaped slider members 86 that are slidingly cooperating with corresponding grooves provided in each one of the ear cups $154_1$, $154_2$. A plurality of three integrated units $174_1$-$174_3$ is fixedly attached to each slider member 86. The ring-shaped slider members 86 are locked in the corresponding grooves by friction and can be moved by an operator to optimize positions of the integrated units by manually applying a force exceeding the friction holding force to the slider members 86.

Another alternative embodiment of patient headphones 250 is shown in FIG. 6. The patient headphones 250 include two holder members (only one holder member shown, other holder member is identically designed and furnished) that are designed as rigid bars 88 attached to one of the ear cups 254 by an articulation 90. One integrated unit 274 is fixedly attached to each rigid bar 88. The rigid bars 88 are held in position by friction force and can be moved about an articulation axis 92 by an operator to optimize positions of the integrated units 274. As an additional option, the articulation 90 might be supported in the ear cup 254 by a bearing which enables to rotate the rigid bar 88 about another articulation axis (not shown) that is arranged perpendicularly to the articulation axis 92 and perpendicularly to the drawing plane of FIG. 6.

Another alternative embodiment of patient headphones 350 is shown in FIG. 7. The patient headphones 350 include two holder members (only one holder member shown, other holder member is identically designed and furnished). Each holder member is designed as two linked rigid bars 94, 96 that are mutually connected at one of their ends by a first articulation 98. The other end of one of the two rigid bars 94, 96 is attached to one of the ear cups 354 by a second articulation 100. A plurality of four integrated units $374_1$-$374_4$ is fixedly attached to and arranged as an evenly spaced array along the rigid bar 96 that is distal to the ear cup 354. The rigid bars 94, 96 are held in position by friction force and can be moved about two articulation axes by an operator to optimize positions of the integrated units $374_1$-$374_4$.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

| REFERENCE SYMBOL LIST | |
|---|---|
| 10 | medical imaging modality |
| 12 | scanning unit |
| 14 | main magnet |
| 16 | examination space |
| 18 | center axis |
| 20 | subject of interest |
| 22 | magnetic gradient coil system |
| 24 | radio frequency shield |
| 26 | control unit |
| 28 | digital memory unit |

| REFERENCE SYMBOL LIST | |
|---|---|
| 30 | processor unit |
| 32 | touch screen device |
| 34 | signal processing unit |
| 36 | radio frequency antenna device |
| 38 | radio frequency transmitter unit |
| 40 | radio frequency switching unit |
| 42 | examination table |
| 44 | table top |
| 46 | induction means (table) |
| 48 | patient headphones system |
| 50 | patient headphones |
| 52 | frame member |
| 54 | ear cup |
| 56 | radio frequency audio transmitter |
| 58 | audio receiving member |
| 60 | sensor system |
| 62 | induction means (headphones) |
| 64 | optical emitter |
| 66 | optical axis |
| 68 | optical sensor |
| 70 | optical axis |
| 72 | radio frequency data emitter |
| 74 | integrated unit |
| 76 | data acquisition and analysis unit |
| 78 | radio frequency data receiver |
| 80 | trigger output signal |
| 82 | software module |
| 84 | fixation clamp |
| 86 | slider member |
| 88 | rigid bar |
| 90 | articulation |
| 92 | articulation axis |
| 94 | rigid bar |
| 96 | rigid bar |
| 98 | first articulation |
| 100 | second articulation steps of |
| 104 | acquire output signals |
| 106 | determine threshold values |
| 108 | define criterion |
| 110 | acquire output signals |
| 112 | apply criterion |
| 114 | generate trigger output signal |
| 116 | gate scanning process |

The invention claimed is:

1. Patient headphones for use in a magnetic resonance imaging system, the patient headphones comprising:
   a frame adapted to fit a head of a patient;
   two ear cups attached to the frame such that, in an operational state of the patient headphones, the ear cups are arranged to be in contact with ears of the patient, respectively; and
   a plurality of integrated units temporarily fixedly attachable to at least one of the frame or the ear cups, using slider connectors or rigid bars, such that the integrated units are moveable to positions relative to the head of the patient while remaining attached to the at least one of the frame or the ear cups, each of the integrated units comprising:
      an optical emitter configured for directing electromagnetic radiation to a portion of skin of the patient;
      an optical sensor configured for receiving at least a portion of the electromagnetic radiation being returned from the portion of the patient's skin, and for providing an output signal that corresponds to the received electromagnetic radiation, wherein an optical axis of the at least one optical emitter intersects an optical axis of the at least one optical sensor at the portion of the patient's skin, and wherein the output signal is indicative of at least one physiological parameter of the patient and serves as a basis for determining the at least one physiological parameter of the patient; and
   a radio frequency data emitter for transmitting the output signal provided by the optical sensor to a data receiver in communication with a processor, wherein the processor analyzes the output signal by applying pre-determined criteria and provides a trigger output signal when one of the pre-determined criteria is fulfilled for controlling a scanning process by the magnetic resonance imaging system.

2. The patient headphones of claim 1, further comprising:
   at least one loudspeaker; and
   an audio receiver configured for receiving an audio signal for driving the at least one loudspeaker.

3. The patient headphones of claim 1, wherein the optical sensor of each of the integrated units comprises a digital camera.

4. A medical imaging modality configured for contact-free acquisition of scanning data of at least a portion of the patient, the medical imaging modality comprising:
   a scanner including an examination space for arranging at least the portion of the patient within;
   a signal processor programmed to generate scanning images from the acquired scanning data; and
   the patient headphones of claim 1.

5. The medical imaging modality as claimed in claim 4, wherein the scanning data are formed by magnetic resonance signals and the generated scanning images are formed by magnetic resonance images, the scanner further including:
   a main magnet configured for generating a static magnetic field $B_0$ at least in the examination space, wherein the examination space is provided in a bore region of the main magnet;
   a magnetic gradient coil configured for generating gradient magnetic fields superimposed to the static magnetic field $B_0$;
   at least one first radio frequency antenna configured for applying a radio frequency excitation field $B_1$ to nuclei of or within the portion of the patient for magnetic resonance excitation; and
   at least one second radio frequency antenna configured for receiving magnetic resonance signals from the nuclei of or within the portion of the patient that have been excited by applying the radio frequency excitation field $B_1$.

6. A method of determining, by using the patient headphones as claimed in claim 1, at least one physiological parameter of a patient to be examined by the magnetic resonance imaging system for gating a scanning process of the magnetic resonance imaging system, the method comprising:
   performing calibration by acquiring the output signal of the optical sensor of each of the integrated units that is indicative of the at least one physiological parameter;
   determining values related to the output signal that are to be used as threshold values;
   defining at least one criterion related to the output signal with regard to the determined threshold values;
   acquiring the output signal of the at least one optical sensor;
   applying the defined at least one criterion to the acquired output signal;
   generating the trigger output signal when the at least one defined criterion is fulfilled; and gating the scanning process using the generated trigger output signal.

7. A non-transitory computer readable medium that stores instructions that, when executed by the processor, cause the processor to carry out the method set forth in claim 6.

8. A patient headphones system for use in a magnetic resonance imaging system, the patient headphones system comprising:
    patient headphones comprising:
        a frame configured to fit a head of a patient;
        an ear cup attached to the frame and configured to contact an ear of the patient; and
        an integrated unit temporarily fixedly attachable to at least one of the frame or the ear cup, using a slider connector or a rigid bar, such that the integrated unit is moveable to positions relative to the head of the patient while remaining attached to the at least one of the frame or the ear cup, the integrated unit comprising:
            an optical emitter and configured to direct electromagnetic radiation to skin of the patient; and
            an optical sensor configured to receive at least a portion of the electromagnetic radiation being returned from the patient's skin, and to provide an output signal corresponding to the received electromagnetic radiation, the output signal indicating a physiological parameter of the patient, wherein an optical axis of the at least one optical emitter intersects an optical axis of the at least one optical sensor at the patient's skin; and
    a control unit having a memory and a processor, the memory storing program code that, when executed by the processor, cause the control unit to perform a process comprising:
        applying pre-determined criteria to the output signal; and
        providing a trigger output signal for controlling a scanning process of the magnetic resonance imaging system when one of the pre-determined criteria is met.

9. The patient headphones system of claim 8, further comprising:
    a radio frequency data receiver configured to receive the output signal by wireless transmission from the patient headphones, and to provide the received output signal to the control unit.

10. The patient headphones system of claim 8, the patient headphones further comprise:
    an additional integrated unit permanently fixed to the ear cup, the additional integrated unit comprising an additional optical emitter configured to direct electromagnetic radiation to skin of the patient, and additional optical sensor configured to receive at least a portion of the electromagnetic radiation being returned from the patient's skin to provide an additional output signal corresponding to the received electromagnetic radiation, the output signal indicating another physiological parameter of the patient, and
    wherein the program code, when executed by the processor, further cause the control unit to perform a process comprising:
        applying pre-determined criteria to the additional output signal; and
        providing another trigger output signal when one of the pre-determined criteria is met for controlling the scanning process.

11. The patient headphones of claim 1, further comprising:
    wherein the slider connectors are configured to slidingly cooperate with corresponding grooves in the ear cups, respectively, wherein the plurality of integrated units are attached to the slider connectors, such that the integrated units are moveable to positions relative to the head of the patient through sliding operations of the slider connectors.

12. The patient headphones of claim 1, further comprising:
    wherein the rigid bars are rotatably attached to the ear cups, respectively, by corresponding articulation joints, wherein the plurality of integrated units are attached to the rigid bars, such that the integrated units are moveable to positions relative to the head of the patient through rotations of the rigid bars.

13. The patient headphones of claim 1, wherein the rigid bars comprise:
    first rigid bars rotatably attached to the ear cups, respectively, by corresponding first articulation joints; and
    second rigid bars rotatably linked to the first rigid bars, respectively, by corresponding second articulation joints,
    wherein the plurality of integrated units are attached along the second rigid bars, such that the integrated units are moveable to positions relative to the head of the patient through rotations of the first and second rigid bars.

14. The patient headphones of claim 1, further comprising:
    at least one permanent integrated unit permanently attached to at least one of the frame or the ear cups, the at least one permanent integrated unit comprising:
        an additional optical emitter configured for directing electromagnetic radiation to another portion of skin of the patient;
        an additional optical sensor configured for receiving at least a portion of the electromagnetic radiation being returned from the another portion of the patient's skin, and for providing another output signal that corresponds to the received electromagnetic radiation, wherein the another output signal is indicative of the at least one physiological parameter of the patient; and
        another radio frequency data emitter for transmitting the another output signal to the data receiver, wherein the processor further analyzes the another output signal and provides the trigger output signal further in response to the analysis of the another output signal.

15. The patient headphones system of claim 8, wherein the patient headphones further comprise:
    wherein the slider connector is configured to slidingly cooperate with a corresponding groove in the ear cup, wherein the integrated unit is attached to the slider connector, such that the integrated units are moveable to positions relative to the head of the patient through a sliding operation of the slider connector.

16. The patient headphones system of claim 8, wherein the patient headphones further comprise:
    wherein the rigid bar is rotatably attached to the ear cup by an articulation joint, wherein the integrated unit is attached to the rigid bar, such that the integrated units are moveable to positions relative to the head of the patient through rotation of the rigid bar.

17. The patient headphones system of claim 8, wherein the rigid bar comprises:

a first rigid bar rotatably attached to the ear cups by a first articulation joint;

wherein a second rigid bar is rotatably linked to the first rigid bar by a second articulation joint; and wherein the integrated unit is attached along the second rigid bar, such that the integrated units are moveable to positions relative to the head of the patient through rotation of the first and second rigid bars.

* * * * *